United States Patent [19]

Cosyns et al.

[11] 4,324,938
[45] Apr. 13, 1982

[54] PROCESS FOR UPGRADING $C_4$ OLEFINIC CUTS

[75] Inventors: Jean Cosyns, Maule; Bernard Juguin; Jean-François Le Page, both of Rueil-Malmaison; Jean Miquel, Paris, all of France

[73] Assignee: Institut Francais du Petrole, Rueil-Malmaison, France

[21] Appl. No.: 180,203

[22] Filed: Aug. 21, 1980

[30] Foreign Application Priority Data

Aug. 21, 1979 [FR] France .............................. 79 21208

[51] Int. Cl.³ .............................................. C07C 1/00
[52] U.S. Cl. ..................................... 585/332; 585/329; 585/331
[58] Field of Search .......................... 585/329, 331, 332

[56] References Cited

U.S. PATENT DOCUMENTS

| | | | |
|---|---|---|---|
| 2,314,435 | 3/1943 | Allender | 585/303 |
| 2,594,343 | 4/1952 | Pines | 260/683.4 |
| 3,409,540 | 11/1968 | Gould et al. | 585/319 |
| 4,242,530 | 12/1980 | Smith | 585/510 |

FOREIGN PATENT DOCUMENTS 2017746 10/1979 United Kingdom.

Primary Examiner—Curtis R. Davis
Attorney, Agent, or Firm—Millen & White

[57] ABSTRACT

Process for upgrading an olefinic $C_4$ cut issued from a cracking or steam cracking unit, comprising subjecting said cut to isomerization conditions so as to convert at least 80% of its 1-butene content to 2-butenes, subjecting the so-treated $C_4$ cut to polymerization conditions so as to convert at least 90% of its isobutene content to isobutene dimers and trimers without substantially converting the normal butenes, separating the isobutene dimers and trimers, alkylating the remaining fraction and fractionating the latter to an alkylate, L P G and an isobutane containing fraction.

13 Claims, 1 Drawing Figure

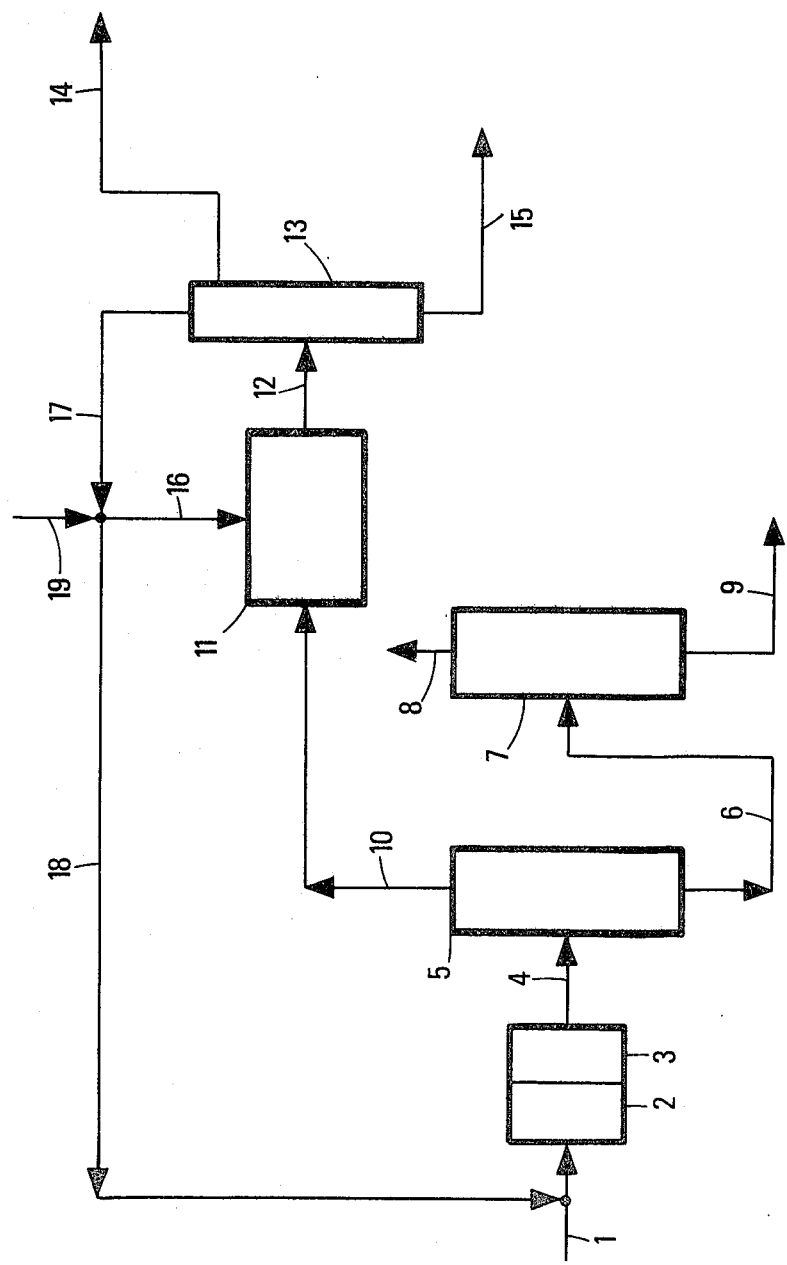

PROCESS FOR UPGRADING $C_4$ OLEFINIC CUTS

BACKGROUND OF THE INVENTION

The development of various processes of steam cracking and catalytic cracking of naphthas and gas-oils results in the supply on the market of a $C_4$ cut which, after butadiene extraction, essentially contains a mixture of butenes, isobutene, butane and isobutane which it is desirable to upgrade.

The olefins, butenes and isobutene can be used for the synthesis of more elaborated petrochemical products (alcohols, aldehydes, acids, nitriles, etc.), but the available amounts of these $C_4$ cuts are generally too large or at least may become too large for having recourse only to this way to upgrade the $C_4$ cuts.

A second way consists of recycling said $C_4$ cut to the cracking unit (steam cracking) or to the catalytic cracking unit, after hydrogenation of the olefins; but, in this case, the isobutane contained in the hydrogenated cut, which amounts to more than 50% by weight of said cut, does not give sufficient ethylene yields and also results in a substantial production of methane which practically can be used only as fuel.

A third way to upgrade said $C_4$ cut consists, after hydrogenation thereof, of separating the n-butane from the isobutane by distillation and recycling to the steam-cracking unit only the n-butane, while recovering the isobutane for more advantageous uses, such for example as the production, by alkylation, of isoparaffinic gasolines. However, the yields of ethylene and propylene in a steam-cracking unit conducted in this manner, do not exceed respectively 38 and 20% by weight and the methane production amounts to about 25% by weight.

A fourth way of upgrading the $C_4$ cut consists of alkylating the olefins of said cut with the isobutane contained therein, so as to obtain the maximum yield of gasoline. However, in said alkylation step, the behaviour of isobutene is less favorable than that of the butenes for obtaining gasoline of high octane number; as a matter of fact, the Research (or Clear) octane numbers of the normal butene alkylates are higher than those of the isobutene alkylates.

In order to improve this fourth way, it is possible, in a first stage, to subject the $C_4$ cut to polymerization during which an effort is made to limit the total conversion of the normal butenes contained in the cut to less than 10% and during which at least 90% of the isobutene is converted (preferably, at least 92% of the isobutene is converted); this hydrocarbon is converted essentially to isobutene dimers and trimers; subsequently, the resulting product is subjected to a fractionation so as to obtain, on the one hand, a first fraction which is fed to the alkylation unit and, on the other hand, a second fraction which is supplied to the gasoline pool, after partial or total hydrogenation thereof. The first fraction, fed to the alkylation stage contains in major part butane and isobutane and the butenes which have not reacted during the polymerization. Such a process is described in the British patent specification No. 2,017,746.

DETAILED DISCUSSION

The present invention is an improvement to the process disclosed in the British patent specification No. 2,017,746 for upgrading the $C_4$ cut, and consists of subjecting the $C_4$ olefinic cut, not to a mere polymerization reaction as above-described, but to a so-called "isomerizing polymerization", which reaction provides not only for a selective conversion of isobutene to $C_8$ dimers and $C_{12}$ trimers, but also for the displacement of the double bond of 1-butene, whereby the major part of 1-butene is converted to 2-butenes, thereby obtaining, under the selected operating conditions and catalysts, a composition close to that corresponding to the thermodynamic equilibrium. The other constituents of the charge are not substantially converted during the isomerization reaction. This conversion of 1-butene to 2-butenes is of prime importance for the alkylation reaction performed after the fractionation of the polymerization effluent, since the products obtained by alkylation of 2-butenes have an octane number clearly higher than that of the alkylates issued from 1-butene (the alkylates obtained from 2-butenes have a R.O.N. from 5 to 7 points higher than that obtained from 1-butene).

The operating conditions are such that the normal butenes contained in the fraction fed to the alkylation zone contain by weight at least 85% of 2-butene and that, during the isomerization, at least 80% of the 1-butene is converted to 2-butenes.

The process according to the invention is diagrammatically illustrated by the accompanying drawing. By the process of the invention, it is possible to obtain a polymerizate which does not require any partial or total hydrogenation, in view of the high quality of said polymerizate.

The hydrogen feeding duct is not shown.

The olefinic $C_4$ cut is fed, through line 1, to the hydroisomerization zone 2 where the isomerization of the double bond of the normal butenes is effected. This hydro-isomerization is performed in the presence of a catalyst used as a fixed bed or a moving bed or a fluidized bed, at a temperature from about 0° to 250° C., under a pressure from about 0.1 to 20 MPa and at a liquid hydrocarbon flow rate (space velocity) of about 0.2 to 20 volumes of hydrocarbon per volume of catatlyst and per hour. The catalyst contains generally at least one metal, preferably from group VIII of the periodic classification of elements (for example cobalt, nickel, palladium, etc.) deposited on a carrier of low acidity, for example transition alumina, silica, etc . . . having a specific surface from about 20 to 300 m² per gram and a pore volume from about 0.20 to 0.80 cc per gram.

The acidity of the carrier may be determined by the known test of ammonia adsorption, described in "Journal of Catalysis, 2, 211-222 (1963): this method consists of heating the carrier to 600° C. under vacuum (i.e. under a pressure lower than about 1 Pa) up to a complete gas removal; then, the carrier is placed in a calorimeter at 320° C. and ammonia is introduced in such an amount that the final pressure of the system at equilibrium attains 40 k Pa and the evolved heat is then measured.

The selected carriers have a neutralization heat, by ammonia adsorption, of less than 10 calories per gram at 320° C. under a pressure of 40 k Pa and preferably less than 7 calories per gram. The neutralization heat of the final catalyst is substantially identical, i.e. less than 10 calories per gram and, preferably, less than 7 calories per gram.

The catalyst may optionally operate in sulfided medium (for inhibiting the hydrogenation properties of the metal), but this is not obligatory. In order to avoid a loss in the catalytic properties of the solid and also to avoid secondary reactions, it is preferable to conduct the reaction under a hydrogen partial pressure, the hydrogen being introduced with the charge. The ratio hydrogen/hydrocarbon is then generally from 0.01 to 2 (ratio expressed in moles per mole).

At the outlet of the hydro-isomerization zone 2, the totality of the effluent enriched with 2-butene (>85% of 2-butene with respect to the total contact of normal butenes in said effluent) is fed to a polymerization zone 3 which may be located either in a second reactor, after the isomerization reactor 2, or in the reactor already used for the isomerization, the separate isomerization and polymerization catalyst beds being then generally superposed.

It must be observed that the effluent from the hydro-isomerization zone contains a hydrogen excess which has not been used during the isomerization and said hydrogen excess also passes through the polymerization zone without producing any disturbance of said polymerization reaction.

In the polymerization zone, the conditions are such that the isobutene reacts up to conversion rates higher than 90% by weight while the total conversions of normal butenes (1-butene and cis-and trans-2-butenes) remain lower than or equal to 10% by weight and preferably lower than 7%.

The polymerization reactions are generally performed in the presence of a catalyst used, for example, in a fixed bed, at a temperature of from about 30° to 400° C., under a pressure from about 0.1 to 20 MPa (1 to 200 bars), (preferably the temperature is from about 80° to 150° C. and the pressure from 2 to 6 MPa) at a liquid hydrocarbon flow rate (space velocity) of from about 0.05 to 5 volumes per volume of catalyst and per hour.

The acid type catalyst may be a silica-alumina or a boron alumina or a borated alumina. It is also possible to select a catalyst obtained by treatment of a transition alumina with an acid fluorine derivative, optionally with the addition of a silicic ester. According to the present invention, the catalyst used in the polymerization reaction exhibits qualities superior to those of other polymerization catalysts such as phosphoric acid on Kieselguhr or on silica, or on quartz, or such catalysts as those of the "solid phosphoric acid" type, i.e. catalysts consisting of a siliceous material of high adsorpting power, impregnated with a high proportion of phosphoric acid, or catalysts such as alumina and thoria gel mixtures, either co-precipitated or not, with optional additions of chromium oxide, zinc oxide or oxide of an equivalent metal.

Preferably, according to the invention, there is used silica-alumina whose silica content is from 60 to 95% by weight and preferably from 70 to 90%, and preferably containing as additive from 0.1 to 5% by weight of zinc oxide. In view of the high exothermicity of the conversion, it is preferable that the isobutene content of the charge be lower than about 35% by weight, since otherwise the charge must be diluted for example with butene or isobutane, and/or, for example, with a portion or the totality of the butane and/or the isobutane issuing through line 17 from the effluent of the hereunder-defined alkylation zone 11. This recycled fraction of butane and/or isobutane is fed either to the polymerization zone 3, when the polymerization reactor is independent from the isomerization reactor 2, or (as shown in the figure) at the inlet of the combined reactor. In the case of a combined reactor with two different beds, one for hydro-isomerization and the other for polymerization, the recycled portion may be supplied directly to the inlet of said second catalyst bed so as to avoid too high a temperature increase.

Preferably, the temperatures, pressures and VVH are substantially the same in the hydro-isomerization and polymerization reaction zones. At the outlet of the polymerization zone, the totality of the reaction mixture i.e. unconverted butenes, unconverted isobutene, isobutene dimers and trimers, butane and dilution butane, isobutane, etc., are conveyed through line 4 to a fractionation zone 5 wherefrom there are withdrawn mainly, through line 10, a first fraction containing a major part of the butane, the isobutane, the isobutene and the butenes and through line 6, a second fraction mainly containing isobutene dimers and trimers. This second fraction is fed to a second fractionation zone 7, wherefrom is withdrawn, at the top, through line 8, a mixture or "poly" gasoline containing a major portion of isobutene dimers and trimers (30 to 70% by weight of dimers and 70 to 30% by weight of trimers, the proportions being expressed in percent of said mixture) which is fed, without requiring hydrogenation, to the gasoline pool, and at the bottom, through line 9, a residue having an initial boiling point higher than 200° C. which can be fed to a fuel oil pool. The fraction withdrawn through line 10 from the fractionation zone 5 is fed to an alkylation zone 11.

Generally, the alkylation reaction is performed either in the presence of a dissolved catalyst, i.e. in liquid phase, or in the presence of a solid catalyst, preferably used as a fixed bed, at a temperature from −20° to 200° C. and under a pressure from 10 kPa to 20 MPa. It is thus possible to proceed in the liquid phase in the presence of a strong inorganic acid such as hydrofluoric acid or sulfuric acid, with or without addition of a Lewis acid such as boron trifluoride or antimony pentafluoride or alternatively, aluminum trichloride, and/or in the optional presence of a Broönsted acid. It is even possible to proceed in the vapor phase in the presence of a solid catalyst of the type of the phosphates, arsenates or stannates of polyvalent metals with boron trifluoride added thereto. Alkylation processes are also known, which are performed in the presence of catalysts having a zeolite structure, with molecular sieves, in the presence of absence of silica-aluminas, for example with the optional presence of at least one metal such as nickel, palladium, rhodium, platinum, etc.

More particularly, the alkylation reaction may be performed at temperatures close to room temperature and under moderate pressures.

An additional isobutane amount can be added to the alkylation zone 11 through line 16. This additional amount is preferable in order to obtain, at the inlet of the alkylation zone, a suitable molar ratio isobutane/olefins in the range from 6/1 to 10/1, this ratio being selected to obtain an alkylate of optimum octane number. The isobutane of line 16 comes from line 17 and/or 19.

There is no obtained, during the alkylation, an alkylate which is withdrawn from line 12 and which can be fractionated in zone 13 in order to obtain:

(a) LPG, which are withdrawn through line 14, usually containing saturated hydrocarbons (iso and normal paraffins) having 4 carbon atoms per molecule, i.e. butanes of high isobutane content, which can be fed to the gasoline pool.

(b) An optional fraction (line 17) of high isobutane content, withdrawn from the top of the fractionation zone 13 and which is fed, according to the needs, to the polymerization zone 3, through line 18 (on the figure line 18 is connected to the inlet of the isomerization zone 2 as above-mentioned) so as to avoid therein too high temperature increases and/or to the alkylation zone 11, through line 16 and, (c) An alkylate which can be used, for example, as motor fuel, since the alkylation products generally have a clear octane number from 88 to 95. This alkylate is recovered through line 15.

Additional isobutane (necessary for diluting the charge and for diluting the cut fed to the alkylation zone) may be introduced through line 19.

According to a preferred embodiment of the invention, the alkylate of line 15 and the "poly" gasoline of line 8 are collected together.

EXAMPLE 1

This example relates to the treatment of an olefinic $C_4$ cut from steam cracking; the charge composition is given in Table I.

TABLE I

| CHARGE COMPOSITION (% BY WEIGHT) | |
|---|---|
| Isobutane | 2 |
| N-butane | 10 |
| Isobutene | 46 |
| 1-butene | 24 |
| 2-butenes | 18 |

This charge is treated in an isomerizing polymerization zone consisting of two successive catalyst fixed beds (2 and 3 in the figure); in the first bed, where the hydro-isomerization takes place, the catalyst is that commercialized under reference LD 265 by Protacalyse Corporation; this catalyst is made of alumina of high purity containing 0.3% by weight of palladium. Its specific surface is 60 m²/g, its total pore volume is 0.50 cc/g, its filling density is 0.7 g/cc. It has the form of balls of a diameter of 2 to 4 mm. The neutralization heat of this catalyst, measured under the above-mentioned conditions, is 6 calories per gram.

In the second bed, where the polymerization takes place, the catalyst is a silica-alumina sold in the trade as being of the Durabead Perl Catalysator Neu type manufactured by Kalichemie Corporation, containing 0.2% by weight of zinc.

The operating conditions, in each of the two isomerization and polymerization zones, are as follows:

| VVH(in $h^{-1}$) | 2 |
|---|---|
| T °C. | 110 |
| Pressure MPa | 4 |

In the hydro-isomerization zone, the ratio $H_2/HC$ is 0.5.

The Table II below reports the composition of the outlet effluent from the isomerization zone as well as the effluent composition at the outlet of the polymerization zone. In the isomerization zone, 82.5% by weight of 1-butene have been converted to 2-butenes.

TABLE II

| | ISOMERIZATION EFFLUENT % b.w. | POLYMERIZATION EFFLUENT % b.w. |
|---|---|---|
| Isobutane | 2 | 2 |
| N-butane | 10 | 10 |
| Isobutene | 46 | 4.5 |
| 1-butene | 4.2 | 3.8 |
| 2-butenes | 37.8 | 34 |
| $C_8$-$C_{12}$ cuts | — | 42.1 |
| (poly) Fuel-oil | — | 3.6 |

After fractionation of the polymerization effluent in zone 5 of the figure, there is recovered, through line 10, normal butane, isobutane, isobutene and 1 and 2-butenes. This fraction is fed to the alkylation zone 11. However, in this cut, the isobutane proportion is insufficient (3.7% of isobutane for 80% of olefins) to obtain a molar ratio isobutane/olefins of at least 6, which is the minimum value required to avoid secondary reactions. Through line 16, there is added an additional amount of isobutane corresponding to 6.2 times the weight of the charge introduced through line 10. The molar ratio isobutane/olefins is then equal to 8.

The alkylation reaction is conducted in the presence of hydrofluoric acid, in reactor 11, stirred and cooled in such a manner as to maintain the temperature of the reaction mixture at 30° C. The other operating conditions are as follows:

pressure: 1.5 MPa
ratio isobutane/olefins: 8 (molar)
hydrofluoric acid volume (at 85% by weight) per hour and per volume of olefin: 2
ratio by volume of acid to hydrocarbons: 1

After decantation, separation, washing and distillation of the reaction effluent, there is obtained (in proportion to the charge fed through line 10):

(1) through line 15: 83.8% by weight (with respect to the initial olefinic $C_4$ cut of line 1) of gasoline alkylate;
(2) through line 14: 10% by weight of LPG containing unreacted butane;
(3) through line 17; the isobutane excess which is recycled, partly to the alkylation zone 11 through line 16, and partly to the polymerization zone 3 through line 18 which, in the embodiment shown in the figure, is connected, as explained above, to the inlet of the isomerization zone and is used to dilute the fresh charge, since the latter contains more than 35% of isobutene as above explained. There is so added to the fresh charge 44.2% by weight of isobutane (dilution isobutane). For sake of simplification of Table II, the dilution isobutane has not been taken into account in the reported results.

Since the charge to be treated in the present example has an insufficient isobutane content, it is necessary to use higher amounts of isobutane by adding isobutane (amounting to 78% by weight with respect to the charge in line 1) through line 19.

The balance of the process with respect to the 100% of the charge and the 44.2% of dilution isobutane, but without taking into account the additional isobutane required in the alkylation reaction (additional amount fed through line 16) is as follows by weight:

| LPG | 10% |
|---|---|
| Alkylate (line 15) | 83.8% |
| "poly" gasoline | 42.1% |

-continued

| | |
|---|---|
| Fuel-oil | 3.6% |
| Products from line 17 | 4.7% |

The obtained gasolines have the following octane numbers:

| | RON | Ethylated RON | MON | Ethylated MON |
|---|---|---|---|---|
| Alkylate | 95 | 108.5 | 91.5 | 106.6 |
| "Poly" gasoline | 102 | 105.5 | 85 | 88 |
| Alkylate and "poly" gasoline mixture | 97.6 | 107.9 | 89.6 | 100.7 |

The octane number of the mixture shows a "synergistic" effect between the components of the mixture, since the theroretical octane numbers are as follows:

RON:
$$95 \times \frac{83.8}{83.8 + 42.1} + 102 \times \frac{42.1}{83.8 + 42.1} = 96.34$$

Ethylated RON:
$$108.5 \times \frac{83.8}{83.8 + 42.1} + 105.5 \times \frac{42.1}{83.8 + 42.1} = 107.50$$

MON:
$$91.5 \times \frac{83.8}{83.8 + 42.1} + 85 \times \frac{42.1}{83.8 + 42.1} = 89.32$$

Ethylated MON:
$$106.5 \times \frac{83.8}{83.8 + 42.1} + 88 \times \frac{42.1}{83.8 + 42.1} = 100.32$$

It is thus preferable to recover together the alkylate and the "poly" gasoline.

EXAMPLE 2

This example concerns the treatment of an olefinic C$_4$ cut from catalytic cracking in the same equipment, under the same conditions, and with the same catalysts as in the preceding example.

The composition in % by weight of said C$_4$ cut is as follows:

| | |
|---|---|
| isobutane | 35 |
| n-butane | 12 |
| isobutene | 16 |
| 1-butene | 10 |
| 2-butenes | 27 |

In the following Table III, the composition of the effluent at the outlet of the hydro-isomerization zone is indicated as well as the composition of the effluent at the outlet of the polymerization zone.

TABLE III

| | ISOMERIZATION EFFLUENT % b.w. | POLYMERIZATION EFFLUENT % b.w. |
|---|---|---|
| isobutene | 35 | 35 |
| n-butane | 12 | 12 |
| isobutene | 16 | 1.5 |
| 1-butene | 3.7 | 3.3 |
| 2-butenes | 33.3 | 30 |
| "poly" gasoline (C$_8$-C$_{12}$) | — | 16.8 |
| fuel-oil | — | 1.4 |

After distillation of the polymerization effluent, there is recovered (a) a "poly" gasoline fraction, (b) a fuel oil fraction and (c) at the top, the olefinic C$_4$ fraction enriched with 2-butenes, which is alkylated by means of isobutane with a ratio iso C$_4$/olefin of 8, obtained by the addition of isobutane, but, in the present example, this isobutane addition is only required for the starting period since the cut contains about enough of isobutane to satisfy the requirement of the alkylation reaction (35% by weight of isobutane for 34.9% of olefin). The other operating conditions are the same as in example 1.

The balance of the process with respect to the 100% of the charge and the 2.8% of dilution isobutane added to the fresh charge through line 18, but without taking into account the additional isobutane required for the alkylation reaction, is as follows by weight:

| | |
|---|---|
| LPG | 12% |
| Alkylate | 68.7% |
| "poly" gasoline | 16.7% |
| Fuel oil | 1.4% |
| Product from line 17 | 4.1% |

The obtained gasolines have the following octane numbers:

| | RON | Ethylated RON | MON | Ethylated MON |
|---|---|---|---|---|
| Alkylate | 95 | 108.5 | 91.5 | 106.5 |
| "Poly" gasoline | 102 | 105.5 | 85 | 88 |
| Alkylate and "poly" gasoline mixture | 96.6 | 108 | 90.5 | 103 |

EXAMPLE 3 (comparative)

The charge of example 1 is treated without making use of the hydro-isomerization zone 2. In other words, the charge passes directly to zone 3 without addition of the hydrogen required for the hydro-isomerization. The other operating conditions are unchanged.

The balance of the process with respect to the totality of the charge (100%) and the 44.2% of dilution isobutane, is given below. The results of example 1 are given in parentheses:

| | | |
|---|---|---|
| LPG | 10 | (10) |
| Alkylate | 80.7 | (83.8) |
| "Poly" gasoline | 42.1 | (42.1) |
| Fuel oil | 3.7 | (3.6) |
| Total products | 136.5 | (139.5) |
| Losses | 7.7 | (4.7) |

Octane number of the obtained product (into brackets, the octane numbers according to example 1):

| | RON | Ethylated RON | MON | Ethylated MON |
|---|---|---|---|---|
| Alkylate | 92.5 (95) | 105.5 (108.5) | 89.5 (91.5) | 104.5 (106.5) |
| "Poly" gasoline | 102 (102) | 105.5 (105.5) | 85 (85) | 88 (88) |
| Alkylate and "poly" gasoline mixture | 95.5 (97.6) | 105.5 (107.9) | 88 (89.6) | 99 (100.7) |

It is observed that the octane numbers of the mixtures are not so good as the calculated theoretical octane numbers of example 1. Furthermore in the present case, it would be more convenient to hydrogenate the "poly" gasoline in order to improve its qualities.

EXAMPLE 4 (comparative)

The charge of example 2 is treated without making use of the hydro-isomerization zone 2. In other words, the charge passes directly to zone 3. The other operating conditions remain unchanged. The balance of the process with respect to the totality of the charge and the 2.9% of dilution isobutane is given below: (in parentheses the results of example 2)

| | | |
|---|---|---|
| LPG | 12 | (12) |
| Alkylate | 67 | (68.7) |
| "Poly" gasoline | 17.1 | (16.7) |
| Fuel-oil | 1.5 | (1.4) |
| Total product | 97.6 | (98.8) |
| Losses | 5.3 | (4.1) |

The obtained gasolines, useful as motor fuel, have the following octane numbers (into parentheses, the octane numbers obtained in example 2):

| | RON | Ethylated RON | MON | Ethylated MON |
|---|---|---|---|---|
| Alkylate | 94 (95) | 107.5 (108.5) | 91 (91.5) | 106 (106.5) |
| "Poly" gasoline | 102 (102) | 105.5 (105.5) | 85 (85) | 88 (88) |
| Alkylated and "poly" gasoline mixture | 95.5 (96.5) | 107 (108) | 90 (90.5) | 102.5 (103) |

The advantage of the process according to the present invention clearly appears from the comparison of the 4 examples. Not only better yields of gasoline, useful as motor fuel, are obtained, but also the obtained gasolines are of higher quality.

What is claimed is:

1. A process for upgrading an olefinic $C_4$ hydrocarbon cracking or steam cracking cut, comprising the steps of:
   (a) feeding the olefinic cut to a hydro-isomerization zone where the cut is treated in the presence of hydrogen and an isomerization catalyst containing at least one group VIII metal, deposited on a carrier, under such conditions that at least 80% of the 1-butene in said cut is isomerized to 2-butenes, the percentages of the other components of the cut being essentially unchanged, and such that, at the end of the isomerization reaction, the normal butenes contained in the hydro-isomerization effluent comprise at least 85% by weight of 2-butenes and less than 15% by weight of 1-butene;
   (b) feeding the entire effluent from the hydro-isomerization zone, without any intermediary fractionation, to a catalytic polymerization zone containing a catalyst different from the hydro-isomerization catalyst, the polymerization catalyst being a fluorinated alumina, a boron alumina, or a silica-alumina, and converting at least 90% of the isobutene contained in the hydroisomerization effluent mainly to isobutene dimers and trimers, the aggregate conversion of the normal butenes contained in the cut being kept lower than or at most equal to 10% by weight, the butene and isobutane contained in the effluent of the hydro-isomerization zone being substantially unconverted;
   (c) fractionating the effluent from the polymerization zone in a fractionation zone and recovering therefrom a first fraction comprising in major part isobutene dimers and trimers, and a second fraction comprising in major part isobutane, butane and butenes; and feeding said second fraction to an alkylation zone, fractionating the alkylation effluent in a fractionation zone, and recovering therefrom (i) an alkylate, (ii) LPG having a high content of saturated $C_4$ hydrocarbons, and (iii) a fraction comprising mainly isobutane.

2. A process according to claim 1, wherein in step (d), the alkylate (i) is combined with the first fraction of isobutene dimers and trimers mixture recovered in step (c), to produce a blended gasoline.

3. A process according to claim 1, wherein the catalyst in the hydro-isomerization zone has a neutralization heat, by ammonia adsorption, lower than 10 calories per gram at 320° C. under a pressure of 40 kPa.

4. A process according to claim 3, wherein the catalyst carrier of the hydro-isomerization zone is alumina.

5. A process according to claim 1, wherein the olefinic $C_4$ cut contains at least about 35% by weight of isobutene, and the cut is diluted with an amount of isobutane sufficient to reduce the proportion of isobutene to below 35% by weight.

6. The process according to claim 1, wherein in step (a), the group VIII metal of the hydro-isomerization catalyst is cobalt, nickel or palladium.

7. A process according to claim 6, wherein the metal is palladium.

8. A process according to claim 1, wherein the hydro-isomerization reaction of step (a) is conducted at a temperature of 0°–250° C., under a pressure of about 0.1–20 MPa, with a liquid hydrocarbons flow rate of about 0.2–20 volumes of hydrocarbons per volume of catalyst and per hour; and wherein the polymerization reaction of step (b) is conducted at a temperature of 30°–400° C., under a pressure of about 0.1–20 MPa, with a liquid hydrocarbons flow rate of about 0.05–5 volumes per volume of catalyst and per hour.

9. A process according to claim 8, wherein the polymerization reaction is conducted at 80°–150° C., under a pressure of 2–6 MPa.

10. A process according to claim 8, wherein the temperature, pressure and hydrocarbons flow rate conditions are substantially the same for the hydro-isomerization as for the polymerization.

11. A process according to claim 5, wherein the isobutane added to dilute the charge is at least a portion of the fraction (iii) comprising mainly isobutane recovered in step (d).

12. A process according to claim 1, wherein in step (d), said second fraction fed to the alkylation zone is diluted with isobutane in an amount sufficient to achieve a molar ratio of isobutane to olefins of 6:1–10:1.

13. A process according to claim 12, wherein the isobutane diluent comprises at least a portion of the fraction (iii) comprising mainly isobutane recovered in step (d).

* * * * *